United States Patent [19]

Archibald et al.

[11] 4,076,820
[45] Feb. 28, 1978

[54] BENZOQUINOLIZINES AND HYPOTENSIVE COMPOSITIONS CONTAINING THEM

[75] Inventors: John Leheup Archibald, Windsor; John Lambert Jackson, Royston, both of England

[73] Assignee: John Wyeth & Brother, Limited, Maidenhead, England

[21] Appl. No.: 685,834

[22] Filed: May 13, 1976

[30] Foreign Application Priority Data

May 22, 1975 United Kingdom ............... 22030/75

[51] Int. Cl.$^2$ ..................... A61K 31/47; C07D 455/06
[52] U.S. Cl. ............................. 424/258; 260/283 SA; 260/283 S; 260/287 CF; 260/288 CF; 260/289 C
[58] Field of Search .................. 260/283 SA, 287 CF, 260/288 CF; 424/258

[56] References Cited

U.S. PATENT DOCUMENTS

| | | | |
|---|---|---|---|
| 3,634,431 | 1/1972 | Van Dyke, Jr. | 260/287 R |
| 3,652,570 | 3/1972 | Gittos et al. | 260/288 R |
| 3,995,041 | 11/1976 | Havera et al. | 424/258 |

Primary Examiner—Alton D. Rollins
Assistant Examiner—Diana G. Rivers
Attorney, Agent, or Firm—Arthur E. Wilfond

[57] ABSTRACT

The invention relates to novel benzoquinolizines of the general formula (I)

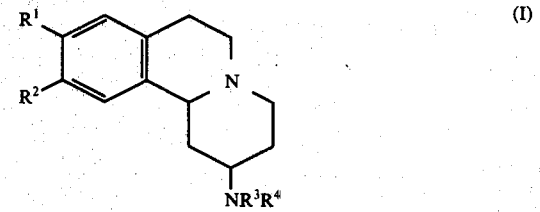

and the pharmaceutically acceptable acid addition salts thereof, wherein $R^1$ and $R^2$ which may be the same or different, each represent hydrogen, lower alkyl, lower alkoxy or halogen, $R^3$ represents hydrogen, lower alkyl or aryl and $R^4$ represents —$SO_2R^5$ (where $R^5$ is lower alkyl or aryl, —$CONH_2$ or —$CXNHR^6$ (where X is oxygen or sulphur and $R^6$ is aryl or aryl.CO.—). The compounds have hypotensive activity.

6 Claims, No Drawings

BENZOQUINOLIZINES AND HYPOTENSIVE COMPOSITIONS CONTAINING THEM

The invention relates to novel heterocyclic compounds, more particularly to novel benzoquinolizines, to processes for preparing the compounds and to pharmaceutical compositions containing them.

The present invention provides novel benzoquinolizines of the general formula (I)

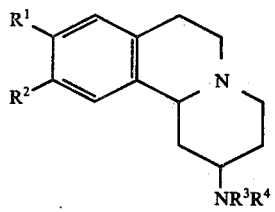   (I)

and the pharmaceutically acceptable acid addition salts thereof, wherein $R^1$ and $R^2$ which may be the same or different, each represent hydrogen, lower alkyl, lower alkoxy or halogen, $R^3$ represents hydrogen, lower alkyl or aryl and $R^4$ represents —$SO_2R^5$ (where $R^5$ is lower alkyl or aryl), —$CONH_2$ or —$CXNHR^6$ (where X is oxygen or sulphur and $R^6$ is aryl or aryl.CO.—).

The term "lower" as used herein means that the radical referred to contains 1 to 6 carbon atoms. Preferably the radical contains 1 to 4 carbon atoms.

When a radical, or part of a radical, is referred to as "aryl" that radical or part of radical is preferably a phenyl or substituted phenyl group. The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), amino, lower alkylamino, diloweralkylamino or trifluoromethyl.

Examples of $R^1$ and $R^2$ are hydrogen, lower alkyl such as methyl, ethyl, propyl or butyl, lower alkoxy such as methoxy, ethoxy, propoxy or butoxy or halogen such as chlorine, fluorine or bromine. $R^1$ and $R^2$ can be different or the same, e.g. they both can be lower alkoxy or preferably hydrogen.

$R^3$ can be hydrogen, lower alkyl (e.g. methyl, ethyl, propyl or butyl) or aryl (e.g. phenyl or substituted phenyl as mentioned above). Preferably $R^3$ is hydrogen.

When $R^4$ represents —$SO_2R^5$, the $R^5$ radical can be lower alkyl (e.g. methyl, ethyl, propyl or butyl) or aryl (e.g. phenyl or substituted phenyl as mentioned above). Preferably $R^5$ is lower alkyl such as methyl.

When $R^4$ represents —$CXNHR^6$, $R^6$ can be, for example, phenyl, substituted phenyl, phenyl.CO— or substituted phenyl.CO—. The substituted phenyl radicals include those mentioned above. $R^4$ can additionally be —$CONH_2$.

A preferred class of compounds are those of general formula (I) wherein $R^1$ and $R^2$ are as defined above, $R^3$ is hydrogen, lower alkyl or phenyl and $R^4$ is —$SO_2R^5$ (where $R^5$ is lower alkyl, phenyl or loweralkylphenyl), —$CONH_2$ or —$CXNHR^6$ (where X is as defined above and $R^6$ is phenyl, trifluoromethylphenyl, loweralkoxyphenyl, halophenyl, loweralkylphenyl or benzoyl).

The compounds of the invention can be prepared by a process in which an amine of general formula (II)

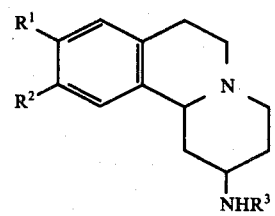   (II)

or an acid addition salt thereof (where $R^1$, $R^2$ and $R^3$ have the meanings given above) is reacted with a reactive derivative of a sulphonic acid compound of general formula (III)

$R^5SO_2OH$   (III)

(where $R^5$ is as defined above) or with an isocyanate or isothiocyanate of general formula (IV)

$R^6NCX$   (IV)

(where X and $R^6$ are as defined above and, if desired, a product of formula I in which $R^4$ represents —CONH-COaryl is hydrolysed to give a product in which R represents —$CONH_2$.

The reaction of the amine of general formula (II) with the reactive derivative of the sulphonic acid compound of general formula (III) gives a compound of the invention in which $R^4$ represents —$SO_2R$. As examples of reactive derivatives of the acid of general formula (III) mention is made of the halide and the anhydride.

Preferably the reactive derivative is a halide i.e. a compound of general formula (IIIa)

$R^5SO_2Y$   (IIIa)

(where $R^5$ is as defined above and Y is halogen, preferably chlorine). The reaction is preferably carried out under basic conditions, for example in the presence of a tertiary amine, e.g. triethylamine. The reactive derivatives of the sulphonic acid compound of general formula (III) are known compounds or they can be prepared by methods known in the art for preparing analogous compounds.

The reaction of the amine of general formula (II) with the isocyanate or isothiocyanate of general formula (IV) gives a compound of the invention in which $R^4$ is —CXNHR. The reaction can be carried out in known manner, e.g. by bringing the reactants together in an inert organic solvent. The isocyanates and isothiocyanates of general formula (IV) are known compounds or they can be prepared by methods known in the art for preparing analogous compounds. In one method of preparing an isothiocyanate of formula (IV) in which X is sulphur and $R^6$ is aryl CO—, a thiocyanate salt (e.g. ammonium thiocyanate) is reacted with an aroyl halide; the product need not be isolated from the reaction mixture but it can be reacted with the amine of general formula (II) in situ to yield a compound of the invention in which $R^4$ is —CSNHCOaryl. Isocyanates of general formula (IV) in which X is oxygen and $R^6$ is arylCO— can be prepared, for example, by the procedure described by Speziale et al., J.Org.Chem., 1962, 27, 3742.

The compounds of the invention in which $R^4$ represents —CXNHaryl can be prepared by an alternative method in which an amine of general formula (V)

arylNH$_2$   (V)

is reacted with an isocyanate or isothiocyanate of general formula (VI)

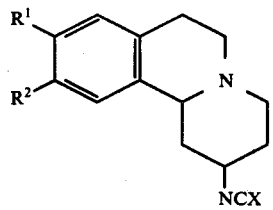
(VI)

(where $R^1$, $R^2$ and X have the meanings given above). The reaction of the amine (V) with the isocyanate or isothiocyanate (VI) is analogous to the reaction of the amine (II) with the isocyanate or isothiocyanate (IV). The amines of general formula (V) are known compounds or they can be prepared by methods known in the art for analogous compounds. The isocyanates or isothiocyanates of general formula (VI) may be prepared by treating an amine of general (II) with phosgene or thiophosgene followed by treatment of the product with calcium oxide.

The compounds of the invention in which $R^4$ represents —$CONH_2$ can be prepared by hydrolysis of the compounds of the invention in which $R^4$ represents —CONHCOaryl. The hydrolysis can, for example, be effected under basic conditions.

If necessary in the reactions hereinbefore described, reactive substituent groups may be protected during a reaction and the protecting group removed at a later stage. Once the compound of general formula (I) has been prepared then if necessary a substituent in the molecule may be converted into another substituent specified in connection with general formula (I).

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The starting amines of general formula (II) in which $R^3$ is hydrogen may be prepared by the following scheme:

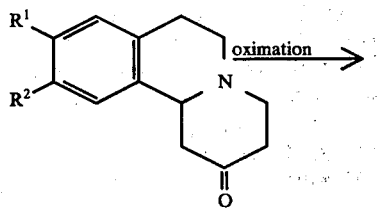
(VII)

(where $R^1$ and $R^2$ have the meanings defined above).

The starting amines of general formula (II) in which $R^3$ is other than hydrogen can also be prepared from the ketones of formula (VII) by the following scheme:

(where $R^1$ and $R^2$ have the meanings given above and $R^7$ is lower alkyl or aryl).

For further details of the preparation of the starting materials by the two schemes shown above and of the preparation of the ketones (VII) reference is made to the procedures described by Van Dyke et al., J. Med. Chem., 1972, 15, 91 and Beke et al., Chem. Ber., 1962, 95, 2132.

The compounds of the invention possess two asymmetric carbon atoms and hence they can exist in various stereochemical forms. In addition they can exist as cis or trans isomers. It will be realised that is the starting material of formula (II) is a mixture of isomers the product of formula (I) will also be a mixture of isomers which can be separated, if required, by standard procedures. If the starting material is a single isomer then the product will also be a single isomer. It is believed that reduction of compound (VIII) with Raney nickel gives essentially trans compound (IX). Other reducing agents can give a mixture of cis and trans products. For a further discussion on some methods of obtaining certain isomers of formula (II) reference is made to the paper by Van Dyke et al mentioned above.

The compounds of the invention exhibit hypotensive activity upon administration to warm-blooded animals as evidenced by a standard pharmacological procedure.

In such a procedure the compounds are administered intravenously to normotensive anaesthetised rats and the fall in diastolic blood pressure is measured 15 minutes after administration. The compounds produce a 30 mm Hg or more fall in blood pressure in this test when administered at a dosage of 25.6 mg/kg. or less. For example, 1-(1,3,4,6,7,11b-hexahydro-2H-benzo[a]quinolizin-2-yl)-3-benzoyl urea, a representative compound of the invention, produced a 30 mm Hg or more fall in blood pressure at a dosage of 6.4 mg/kg, in duplicate experiments.

The invention further provides a pharmaceutical composition which comprises a compound of formula (I) or a pharmaceutically acceptable acid addition thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; it if is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg., according to the particular need and the activity of the active ingredient. The invention also includes the compounds in the absence of carrier where the compounds are in unit dosage form.

The following Examples illustrate the invention:

EXAMPLE 1

1-(1,3,4,6,7,11b-Hexahydro-2H-benzo[a]quinolizin-2-yl)-3-phenyl urea

To 2-amino-1,3,4,6,7,11b-hexahydro-2H-benzo[a]quinolizine (0.436 g) stirred at room temperature in benzene (50 ml) was added phenyl isocyanate (0.290 g, 5% excess) in benzene (25 ml). After stirring for 18 hours, the title compound was filtered off as a white solid (0.621 g) which was converted in ethanolic hydrogen chloride to the hydrochloride (0.654 g), m.p. 210.1° C. $C_{20}H_{23}N_3O.HCl.H_2O$ requires C, 63.90; H, 6.97; N, 11.18% Found: C, 63.72; H, 6.87; N, 11.10%.

EXAMPLE 2

1-(1,3,4,6,7,11b-Hexahydro-2H-benzo[a]quinolizin-2-yl)-3-phenylthiourea

2-Amino-1,3,4,6,7,11b-hexahydro-2H-benzo[a]quinolizine (0.766 g) and phenyl isothiocyanate (0.563 g) were condensed together in benzene (50 ml) in a manner analogous to that of Example 1 to give the title compound (0.724 g). Crystallization from EtOH/HCl afforded the hydrochloride (0.950 g), m.p. 213.5° C. $C_{20}H_{23}N_3S.HCl$ requires C, 64.25; H, 6.47; N, 11.24% Found: C, 63.94; H, 6.56; N, 11.16%.

EXAMPLE 3

1-(1,3,4,6,7,11b-Hexahydro-2H-benzo[a]quinolizin-2-yl)-3-benzoyl urea.

2-Amino-1,3,4,6,7,11b-hexahydro-2H-benzo[a]quinolizine (0.260 g) and benzoyl isocyanate (0.213 g, 5% excess) were condensed together in benzene (50 ml) in a manner analogous to that of Example 1 to give the title compound (0.325 g). Crystallization from EtOH/HCl afforded the hydrochloride (0.343 g). m.p. 171.0° C. $C_{21}H_{23}N_3O_2.HCl.2H_2O$ requires C, 59.78; H, 6.69; N, 9.96%, Found: C, 60.06; H, 6.50; N 9.89%.

EXAMPLE 4

1-(1,3,4,6,7,11b-Hexahydro-2H-benzo[a]quinolizin-2-yl)-3-benzoyl-thiourea

To 2-amino-1,3,4,6,7,11b-hexahydro-2H-benzo[a]quinolizine (2.59 g) stirred at room temperature in benzene (150 ml) was added benzoyl isothiocyanate (2.30 g) in benzene (50 ml). After stirring for 18 hours, the solvent was removed under vacuum and the title compound obtained as the hydrochloride by treating the residue with ethanolic hydrogen chloride in the usual manner, (1.994 g) m.p. 210.8° C. $C_{21}H_{23}N_3OS.HCl.3/4H_2O$ requires C, 60.71; H, 6.18; N, 10.11%. Found: C, 60.63; H, 5.99; N, 10.28%.

EXAMPLE 5

1-(1,3,4,6,7,11b-Hexahydro-2H-benzo[a]quinolizin-2-yl)-3-(2-trifluoromethylphenyl)urea 2-Amino-1,3,4,6,7,11b-hexahydro-2H-benzo[a]quinolizine (0.545 g) and o-trifluoromethylphenyl isocyanate (0.544 g) were condensed together in benzene (50 ml) in a manner analogous to that of Example 4 to give the title compound as the hydrochloride (0.815 g) m.p. 242.1° C. $C_{21}H_{22}F_3N_3O.HCl$ requires C, 59.22; H, 5.44; N, 9.87; Found: C, 59.65; H, 5.41; N, 10.31%.

EXAMPLE 6

1-(1,3,4,6,7,11b-Hexahydro-2H-benzo[a]quinolizin-2-yl)-3-(4-methoxyphenyl)urea

2-Amino-1,3,4,6,7,11b-hexahydro-2H-benzo[a]quinolizine (0.462 g) and p-methoxyphenyl isocyanate (0.375 g) were condensed together in benzene (50 ml) in a manner analogous to that of Example 4 to give the title compound as the hydrochloride (0.632 g) m.p. 245.5° C. $C_{21}H_{25}N_3O_2.HCl$ requires C, 65.02; H, 6.76; N, 10.83%. Found: C, 65.03; H, 6.90; N, 10.73%.

EXAMPLE 7 a.

2-Methanesulphonamido-1,3,4,6,7,11b-hexahydro-2H-benzo[a]quinolizine (isomer 'A')

To 2-amino-1,3,4,6,7,11b-hexahydro-2H-benzo[a]quinolizine hydrochloride (1.38 g), suspended in a solution of triethylamine (2 ml) in dichloromethane (10 ml) stirred at room temperature was added methane sulphonyl chloride (0.570 g) in dichloromethane (5 ml). After stirring for 18 hours, the solution was washed with water and the organic phase separated, dried and evaporated to yield the title compound (1.06 g) as an oil, which was converted in ethanolic hydrogen chloride to the hydrochloride (0.395 g) m.p. 244.8° C. $C_{14}H_{20}N_2O_2S.HCl$ requires C, 53.06; H, 6.68; N, 8.84%. Found: C, 53.07; H, 6.77; N, 8.64%.

b.

2-Methanesulphonamido-1,3,4,6,7,11b-hexahydro-2H-benzo[a]quinolizine (Isomers 'A' and 'B')

A solution of methanesulphonyl chloride (1.9g) in dichloromethane (6 ml) was added dropwise to an ice cooled suspension of 2-amino-1,3,4,6,7,11b-hexahydro-2H-benzo[a]quinolizine dihydrochloride (4.06 g) in a mixture of dichloromethane (30 ml) and triethylamine (8.4 ml). After addition was complete the solution was allowed to stand for 1 hour and then poured into water. The organic phase was separated, dried, and evaporated. The residue was dissolved in ethanol (15 ml) acidified with ethanolic hydrogen chloride and diluted with ethyl acetate (15 ml). On standing overnight a mixture of hydrochlorides of the title compounds separated and was collected by filtration. The mixture was crystallised from methanol to give isomer 'A' hydrochloride (1.9 g, m.p. 251°-4° C). $C_{14}H_{20}N_2O_2S.HCl$ requires C, 53.06; H, 6.68; N, 8.84%. Found: C, 53.09; H, 6.75; N, 8.79%. The product had an IR spectrum corresponding to that of the product of Example 7a. The mother liquors were evaporated, basified with aqueous ammonia, and extracted into chloroform. The extract was dried and evaporated; the residue was then crystallised from acetonitrile (15 ml) to give Isomer 'B' (0.6 g) as the pure free base. The base was dissolved in the minimum quantity of ethanol and acidified with ethanolic hydrogen chloride to yield Isomer 'B' as the hydrochloride, half hydrate (0.6 g), m.p. 248° to 250° C. $C_{14}H_{20}N_2O_2HCl.O.5H_2O$ requires C, 51.60; H, 6.81; N, 8.60%. Found: C, 51.88; H, 6.73; N, 8.34%.

EXAMPLE 8

2-Ethanesulphonamido-1,3,4,6,7,11b-hexahydro-2H-benzo[a]quinolizine (Isomers 'A' and 'B')

2-Amino-1,3,4,6,7,11b-hexahydro-2H-benzo[a]quinolizine dihydrochloride (3.65g) was dissolved in dichloromethane (30 ml), and the solution ice-cooled and stirred whilst a solution of triethylamine (2.83 g) in dichloromethane (10 ml) was added. The ice-cooling and stirring were maintained whilst a solution of ethanesulphonyl chloride (2.20 g) in dichloromethane (10 ml) was added dropwise. The reaction was stirred at room temperature for a further 3 hours before washing the solution twice with aliquots of water (50 ml). The dichloromethane solution was evaporated to yield a yellow oil, which was dissolved in ethanol (10 ml) and ethanol saturated with hydrogen chloride was added dropwise until the solution was acidic (pH2). On standing for 0.1 hour white crystals were produced, which, after standing for a further 0.1 hour were removed by filtration to constitute a first crop. After allowing the filtrate to stand for 1 hour the solution was filtered again to produce a second crop of white crystals. A third crop was obtained by evaporation of the filtrate. Thin-layer-chromatography indicated that two products had been formed. The two products were isolated by fractional crystallisation of the three crops from hot methanol to give chromatographically pure 2-ethanesulphonamido-1,3,4,6,7,11b-hexahydro-2H-benzo[a]quinolizine hydrochloride, isomer A (1.13g) and chromatographically pure 2-ethanesulphonamido-1,3,4,6,7,11b-hexahydro-2H-benzo[a]-quinolizine hydrochloride, isomer B (1.05 g). The isomer A hydrochloride had m.p. 234°–6° C ($C_{15}H_{22}N_2O_2S.HCl$ requires C, 54.45; H, 7.01; N, 8.47%. Found: C, 54.25; H, 6.97; N, 8.18%) and isomer B hydrochloride had m.p. 227°–8° C ($C_{15}H_{22}N_2O_2S.HCl$ requires C, 54.45; H, 7.01; N, 8.47%. Found: C, 54.46; H, 7.09; N, 8.16%).

EXAMPLE 9

2-Phenylsulphonamino-1,3,4,6,7,11b-hexahydro-2H-benzo[a]quinolizine (Isomers 'A' and 'B')

a. 2-Amino-1,3,4,6,7,11b-hexahydro-2H-benzo[a]quinolizine dihydrochloride (2.76 g) and triethylamine (2.22g), dissolved in dichloromethane (20 ml), were stirred with ice-cooling whilst a solution of benzenesulphonyl chloride (1.96g) in dichloromethane (4 ml) was added dropwise. The reaction was then stirred at room temperature for a further 3 hours. The solution was washed twice with water (50 ml) and evaporated, to give a yellow/brown oil. The oil was dissolved in ethanol (10 ml) and stored under vacuum in a silica-gel dessicator for 15 hours. The resulting crystals were removed by filtration and the filtrate retained for Example 9(b). The crystals were washed with a little ethanol, then ether and dried. Purification and conversaion to the hydrochloride were effected by dissolving the crystals in the minimum volume of ethanol and adding a saturated solution of hydrogen chloride in ethanol dropwise until the solution became acidic (pH2). On standing a white precipitate of the hydrochloride of isomer 'A' of the title compound was produced. This was filtered, washed with a little ethanol, then ether, and dried (0.82 g) m.p. 255° C. $C_{19}H_{22}N_2O_2.HCl$ requires C, 60.22; H, 6.12; N, 7.39%. Found: C, 59.68; H, 6.16; N, 7.12%.

b. The filtrate retained from Example 9(a) was acidified to pH2 with a saturated solution of hydrogen chloride in ethanol, left to crystallise for 0.1 hour, and then filtered.

The crystals were washed with ethanol, then ether, and dried. Recrystallisation was effected by dissolving the crystals in chloroform (25 ml) and ¼ strength "0.880" ammonia solution (25 ml), separating the chloroform layer, washing it with water, evaporating to dryness, and converting to the hydrochloride by the method of Example 9(a). Several recrystallisations were necessary to obtain the hydrochloride of isomer 'B' of the title compound in high purity (0.59g) m.p. 245°–6° C. $C_{19}H_{22}N_2O_2S.HCl$ requires C, 60.22; H, 6.12; N, 7.39%. Found: C, 59.92; H, 6.30; N, 6.95%.

EXAMPLE 10

1,3,4,6,7,11b -Hexahydro-2H-benzoquinolizin-2-ylurea 1-(1,3,4,6,7,11b-Hexahydro-2H-benzo[a]quinolizin-2-yl)-3-benzoylurea hydrochloride (0.98 g) was refluxed in 2N sodium hydroxide solution (50 ml) for 4 hours. The solution was filtered and the residue washed with water, then ethanol, and finally ether before drying to give the title compound (0.46 g) melting point 235° C. $C_{14}H_{19}N_3O$ requires: C, 68.54%; H, 7.81%; N, 17.13%. Found: C, 68.53%; H, 7.79%; N, 17.33%.

EXAMPLE 11

1-(1,3,4,6,7,11b-Hexahydro-9,10-dimethoxy-2H-benzo[a]quinolizin-2-yl)-1,3-diphenyl urea By a procedure analogous to that of Example 1, 2-anilino-1,3,4,6,7,11b-hexahydro-9,10-dimethoxy-2H-benzo[a]quinolizine (U.S. Pat. No. 3,634,431) is reacted with phenyl isocyanate to give the title compound.

EXAMPLE 12

1-(1,3,4,6,7,11b-Hexahydro-2H-benzo[a]quinolizin-2-yl)-1-methyl-3-phenyl urea.

By a procedure analogous to that of Example 1, 2-methylamino-1,3,4,6,7,11b-hexahydro-2H-benzo[a]quinolizine (J. Med. Chem., 1972, 15, 91) is reacted with phenyl isocyanate to give the title compound.

EXAMPLE 13

1-(1,3,4,6,7,11b-Hexahydro-2H-benzo[a]quinolizin-2-yl)-3-(2-chlorophenyl)urea

By a procedure analogous to that of Example 1, 2-amino-1,3,4,6,7,11b-hexahydro-2H-benzo[a]quinolizine is reacted with o-chlorophenyl isocyanate to give the title compound.

EXAMPLE 14

1-(1,3,4,6,7,11b-Hexahydro-2H-benzo[a]quinolizin-2-yl)-3-(4-methylphenyl)urea.

By a procedure analogous to that of Example 1, 2-amino-1,3,4,6,7,11b-hexahydro-2H-benzo[a]quinolizine is reacted with p-methylphenyl isocyanate to give the title compound.

EXAMPLE 15

2-p-Tolylsulphonamino-1,3,4,6,7,11b-hexahydro-2H-benzo[a]quinolizine

2-Amino-1,3,4,6,7,11b-hexahydro-2H-benzo[a]quinolizine is reacted with p-toluenesulphonyl chloride by a procedure analogous to that of Example 9 to give the title compound.

EXAMPLE 16

1-(9-Chloro-1,3,4,6,7,11b-Hexahydro-2H-benzo[a]quinolizin-2-yl)-phenyl urea

2-Amino-9-chloro-1,3,4,6,7,11b-hexahydro-2H-benzo[a]quinolizine [prepared from 9-chloro-1,3,4,6,7,11b-hexahydro-2H-benzo[a]quinolizin-2-one (Neth.Appln. No. 6,508,468) by reduction of the oxime] is reacted with phenyl isocyanate by a procedure analogous to that of Example 1 to give the title compound.

EXAMPLE 17

2-Methanesulphonamido-1,3,4,6,7,11b-hexahydro-10-methyl-2H-benzo[a]quinolizine

2-Amino-1,3,4,6,7,11b-hexahydro-10-methyl-2H-benzo[a]quinolizine [prepared from 1,3,4,6,7,11b-hexahydro-10-methyl-2H-benzo[a]quinolizin-2-one (Neth.Appln. No. 6,508,468) by reduction of the oxime] is reacted with methane sulphonyl chloride by a process analogous to that of Example 7(a) to give the title compound.

We claim:

1. A compound selected from the group consisting of a benzoquinolizine of formula

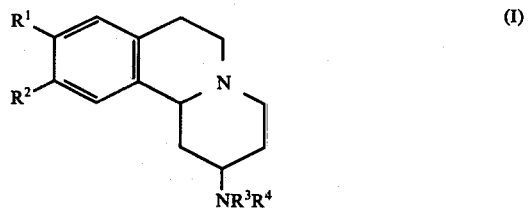

and a pharmaceutically acceptable acid addition salt thereof, wherein $R^1$ and $R^2$ each represents a member from the group consisting of hydrogen, lower alkyl, lower alkoxy and halogen, $R^3$ represents a member of the group consisting of hydrogen, lower alkyl and aryl, $R^4$ represents $—SO_2R^5$ (wherein $R^5$ represents lower alkyl or aryl), and aryl represents phenyl and mono-substituted phenyl, wherein the substituents are selected from halogen, alkoxy, lower alkyl, methylenedioxy, ethylenedioxy, amino, lower alkylamino, dilower alkylamino and trifluoromethyl.

2. A compound selected from the group consisting of a benzoquinolizine of formula

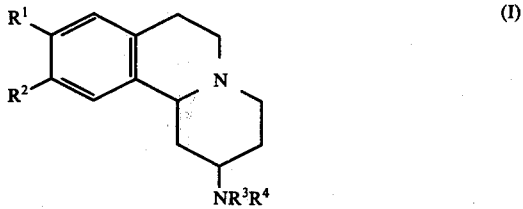

and a pharmaceutically acceptable acid addition salt thereof, wherein $R^1$ and $R^2$ each represents a member from the group consisting of hydrogen, lower alkyl, lower alkoxy and halogen, $R^3$ represents a member of the group consisting of hydrogen, lower alkyl and phenyl, $R^4$ represents $—SO_2R^5$ (wherein $R^5$ represents lower alkyl, phenyl and lower alkylphenyl).

3. A compound as claimed in claim 2, which is 2-methanesulphonamido-1,3,4,6,7,11b-hexahydro-2H-benzo[a]quinolizine.

4. A compound as claimed in claim 2 which is 2-ethanesulphonamido-1,3,4,6,7,11b-hexahydro-2H-benzo[a]quinolizine.

5. A compound as claimed in claim 2 which is 2-phenylsulphonamido-1,3,4,6,7,11b-hexahydro-2H-benzo[a]quinolizine.

6. A hypotensive composition comprising a hypotensively effective amount of a compound selected from the group consisting of a benzoquinolizine of formula

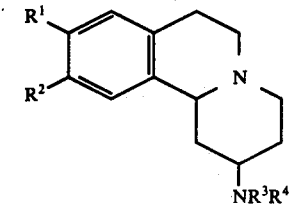

and a pharmaceutically acceptable acid addition salt thereof, wherein $R^1$ and $R^2$ each represents a member from the group consisting of hydrogen, lower alkyl, lower alkoxy and halogen, $R^3$ represents a member of the group consisting of hydrogen, lower alkyl and phenyl, $R^4$ represents —$SO_2R^5$ (wherein $R^5$ represents lower alkyl, phenyl and lower alkylphenyl), in association with a pharmaceutically acceptable carrier.

* * * * *